United States Patent [19]

Gregory et al.

[11] 4,087,330

[45] * May 2, 1978

[54] IMMOBILIZATION OF ENZYMES USING RECYCLED SUPPORT MATERIALS

[75] Inventors: Jerry L. Gregory, Painted Post; Wayne H. Pitcher, Jr., Big Flats, both of N.Y.

[73] Assignee: Corning Glass Works, Corning, N.Y.

[*] Notice: The portion of the term of this patent subsequent to Jul. 18, 1992, has been disclaimed.

[21] Appl. No.: 754,075

[22] Filed: Dec. 23, 1976

Related U.S. Application Data

[63] Continuation-in-part of Ser. No. 597,012, Jul. 18, 1975, Pat. No. 4,002,576.

[51] Int. Cl.$^2$ .............................................. C07G 7/02
[52] U.S. Cl. .................................... 426/68; 195/31 F; 426/63
[58] Field of Search .................. 195/63, 68, DIG. 11, 195/31 F; 134/25 R, 2

[56] References Cited

U.S. PATENT DOCUMENTS

| 3,671,179 | 6/1972 | Jinnette | 134/2 X |
| 3,894,884 | 7/1975 | Druin et al. | 134/25 R |
| 3,965,035 | 6/1976 | Bialousz et al. | 195/63 X |
| 4,002,576 | 1/1977 | Gregory et al. | 195/68 X |

*Primary Examiner*—David M. Naff
*Attorney, Agent, or Firm*—James A. Giblin; Clinton S. Janes, Jr.; Clarence R. Patty, Jr.

[57] ABSTRACT

Immobilized enzyme composites comprising enzymes bonded to porous, high surface area support materials can be economically prepared by contacting "spent" composites with a solution of NaOCl to remove substantially all contaminants resulting from previous use of the composites and then reacting the cleaned support materials with a solution of active enzymes under conditions sufficient to permit the bonding of enzymes to the surfaces of the support materials.

6 Claims, No Drawings

1

IMMOBILIZATION OF ENZYMES USING RECYCLED SUPPORT MATERIALS

RELATED APPLICATION

This application is a continuation-in-part of our pending application Ser. No. 597,012 filed July 18, 1975, now U.S. Pat. No. 4,002,576, and entitled "Enzyme Carrier Regeneration."

BACKGROUND OF THE INVENTION

This disclosure is concerned generally with the immobilization of enzymes using porous, high surface area, water insoluble support materials. The disclosure is specifically concerned with a novel method of recycling the support material of spent immobilized enzyme composites so that the material can be conveniently re-used for enzyme immobilization.

It is known that enzymes can be immobilized by various means using a wide variety of water-insoluble support materials. See, for example, U.S. Pat. No. 3,645,852, to Axen et al. (chemical bonding of enzymes to organic support materials), U.S. Pat. No. 3,519,538 to Messing et al. (chemical bonding of enzymes to inorganic supports), U.S. Pat. No. 3,850,751, to R. A. Messing (adsorption of enzymes to inorganic supports), and U.S. Pat. No. 3,705,084 to Reynolds (chemical bonding to supports including both organic and inorganic materials). In general, many preferred support materials (carriers) are porous and/or have a relatively high surface area (e.g. $> 5$ m$^2$/g) which permits a relatively large amount of enzyme to be loaded onto the carrier.

Even though numerous support materials have been successfully used to prepare immobilized enzyme composites having relatively high enzyme loadings and long enzymatic half-lives, it can be appreciated that the use of such composites, especially the continuous use, is economically time-limited. Regardless of the loading or enzymatic half-life of a given immobilized enzyme composite, it is known that, in use, the total enzymatic activity tends to decline with time. Thus, at a given point in time, it becomes more economical to simply replace "spent" enzyme composite with "fresh" composite.

As used herein, the expression "spent" immobilized enzyme composite, or its equivalent, refers to an immobilized enzyme composite which, after at least some use for its intended purpose, has become uneconomical to use further. The expression "fresh" immobilized enzyme composite refers to such composite which can still be economically used for its intended purpose. Several factors may determine the point in use or time when a given immobilized enzyme system becomes "spent" or uneconomical to use. For example, the enzymatic half life or amount of active enzyme on or within the support may have dropped to a relatively low level. The composite may have become contaminated with microbial growth which precludes further economical use. The composite may become contaminated with an undesirable excess of various metal ions which become associated with the composite after prolonged, continuous use with a substrate solution to which various buffers containing such ions are often added. The enzymes may simply become inactive. Regardless of cause or causes, it can be appreciated that a spent composite can contain a variety of materials both organic (e.g. proteins, microbes) and inorganic (e.g. salts). For purposes of this disclosure, all such materials associated with a spent composite are referred to as contaminants and they include substantially all materials except the support itself.

Although the support materials used for many immobilized enzyme systems are relatively inexpensive and may be discarded after use or when the immobilized enzyme composite is deemed spent, it can be appreciated that in some cases the reuse or recycling of the support materials may offer distinct advantages. For example, the reuse of support materials would not only offer possible cost savings, but also help avoid problems associated with the discharge of spent composites.

It is known that various pyrolysis treatments can be used to burn off organic materials on inorganic supports. However, as pointed out in U.S. Pat. No. 3,965,035, simple pyrolysis does not assure the removal of all contaminants (e.g., various metal ions from substrate solutions) which tend to minimize subsequent enzyme reloading and half life. In the above-cited patent, a two-step method of regenerating an inorganic enzyme carrier is disclosed. In the first step, the spent enzyme composite is pyrolyzed at a temperature ranging from about 500° to 900° C under conditions sufficient to assure removal of substantially all carbonaceous matter. Then, the carrier is reacted with a neutralized citrate solution to assure removal of remaining contaminants. Although the two-step method is quite effective in permitting the recycling of the specific carriers disclosed, it can be appreciated that the method is somewhat cumbersome in that the pyrolysis step generally requires removal of the spent composite from its container (e.g. a flow-through column) and placement in an appropriate furnace, followed by removal from the furnace, replacement in the column and treatment with the citrate solution.

In copending patent application Ser. No. 597,012 entitled "Enzyme Carrier Regeneration" we disclosed that the two-step process of U.S. Pat. No. 3,965,035, could be replaced by a relatively simple one-step regeneration technique which did not require a pyrolysis step. The one-step method involved reacting a specific MgO-Al$_2$O$_3$ support for the enzyme glucose isomerase with a solution of sodium hypochlorite under conditions sufficient to assure removal of all contaminants. Since the disclosure of our copending application, we have found that the disclosed single step technique can be used to recycle other enzyme support materials and thereby provide a relatively simple, economical method of regenerating enzyme supports and preparing fresh immobilized enzyme composites. Details of our methods are disclosed herein.

SUMMARY OF THE INVENTION

Our method of preparing immobilized enzyme composites comprising enzymes bonded to porous, high surface area support materials comprises the steps of contacting spent immobilized enzyme composite with an aqueous NaOCl solution under conditions sufficient to remove substantially all contaminants associated with the composite and resulting from previous use of the composite, and then reacting the cleaned support material of the composite with a solution of enzymes under conditions sufficient to permit the bonding of enzymes to the surfaces of the cleaned support material. Our methods are especially useful for preparing enzymes immobilized by adsorption onto porous inorganic supports which have been made reuseable by reaction with the solution of the sodium hypochlorite.

SPECIFIC EMBODIMENTS

Our method of preparing composites of enzymes immobilized on porous, high surface area support materials comprises two basic steps. In the first step, a spent composite consisting of the support material and associated contaminants including both inactive and active enzymes etc., is reacted with a NaOCl solution under conditions sufficient to remove substantially all contaminants without adversely affecting the support material. The reaction with the NaOCl solution serves to regenerate the support and the regeneration is especially useful with porous inorganic carriers having a very high surface area. The contact of the spent composite with the NaOCl solution can be under any reaction conditions or in any reactor system which permits intimate contact of the NaOCl solution with the surfaces of the carrier being regenerated. In the case of the immobilized glucose isomerase system described below, the support was regenerated by fluidizing the composite particles in a fluidized bed reactor with the NaOCl solution. In the immobilized glucoamylase system, the spent composite was merely contacted (batch reaction) with the NaOCl solution. The immobilized lactase carrier was regenerated using down flow of NaOCl solution through a packed column of the spent composite. As used herein, the expressions react, contact, or their equivalent, when used with reference to the exposure of the spent composite with an NaOCl solution, include all of the above reaction conditions.

In general, the amount of the NaOCl in the solution should comprise at least about 5 times the weight of protein to be removed from the spent composite. It is thought that, given this disclosure, the optimum concentration, reaction time, temperature, etc. for a given spent composite can be readily determined by one skilled in the art. It is also thought that the amount of NaOCl solution of a given concentration used per unit weight or volume of a spent composite can also be determined once the other reaction conditions are known. It should be pointed out that a variety of other agents other than NaOCl were investigated. These included hydrogen peroxide, HCl, sodium, calcium, and magnesium hydroxides, tris buffers, acetate buffers, sodium carbonate, sodium malate, EDTA, sodium phthalate, and sodium citrate. It was found, however, that original enzyme activity could be restored only with the NaOCl solutions, at least for the glucose isomerase system.

The second step of our method involves reacting the regenerated support material with a fresh enzyme solution under conditions sufficient to permit the bonding of at least some active enzyme onto the high surface area support. In the examples below, porous, high surface area inorganic supports which had been exposed to the NaOCl solution were then exposed to an aqueous solution of active enzymes to permit bonding of enzymes to the carrier via simple adsorption. The inorganic supports had average pore sizes ranging from about 190 to 370A and average particle sizes ranging from about 30 to 45 mesh, U.S. Standard Sieve. Although the ideal enzyme bonding technique may vary from system to system, we found that excellent results were obtained by reacting about 15 g of support with about 30 ml of enzyme solution for about 24 hours at room temperature.

In the illustrative examples below, enzymes were successfully bonded to porous inorganic supports using spent composite supports which had been cleaned by reaction with the NaOCl solution under the conditions indicated. In the first three systems using the recycled support, the before and after enzyme loadings, as measured in activity units of enzyme per gram of composite, were substantially the same, thus confirming the utility of the regeneration step. In a fourth system in which the enzyme was covalently bonded to the support via an intermediate silane coupling agent, the silane did not appear to be removed by the stripping action of the NaOCl reaction. In the subsequent step of loading the enzyme via adsorption, it was found that the amount of enzyme loaded was only slightly more than one half of that originally on the support. Although these recycling results were not as good as those observed for the originally adsorbed system, the data did show that, to a limited extent, the supports of chemically coupled spent composites could be recycled.

EXAMPLE I

Glucose Isomerase Adsorbed to Recycled $MgO\text{-}Al_2O_3$ Carrier

In this example, the $MgO\text{-}Al_2O_3$ carrier consisted of 30 to 45 mesh porous particles having an average pore diameter ranging from about 190A to 210A and consisting of about 2.2% by weight MgO. This carrier is described in U.S. Pat. No. 3,992,329. A one time "use" of the immobilized glucose isomerase using such carrier consisted of placing in columns about 15 g quantities of the composite consisting of the glucose isomerase adsorbed to the $MgO\text{-}Al_2O_3$ particles in accordance with the directions of the above patent and then continuously passing a glucose-containing solution through the column at a flow rate of about 3 to 4 ml per min. The glucose solutions contained 0.005 M $MgCl_2$ and was buffered to a pH of about 8.4. Each column was deemed "spent" after having been used for an enzymatic half life of the composite (about 30 days). Glucose isomerase activity was measured in International Glucose Isomerase Units (IGIU) in accordance with the method described more fully in U.S. Pat. No. 3,992,329.

In the experiments, spent enzyme composites were regenerated by circulating varying amounts and concentrations of an aqueous NaOCl solution through the columns containing the spent immobilized enzyme. The amounts of composite in each column ranged from about 15 g at start down to about 4 g with the successive regenerations. In the regeneration steps, the goal is to provide a reusable carrier capable of as high an enzyme re-loading as possible. To be economically feasible, we found that glucose isomerase composites should demonstrate an in use loading of about 600 IGIU per gram of composite. Hence, any regeneration of carrier which could assure such loading can be deemed successful.

It was found that to a limited extent, the amount of NaOCl solution used in the regeneration had some effect on subsequent enzyme reloading. Preferably, at least about 5 ml of a 5% NaOCl solution is used per gram of carrier to be regenerated. As the amount of NaOCl solution was increased, it was found that there occured an increase in enzyme reloading. For example, in one set of experiments about 1800 IGIU of enzyme was offered per gram of carrier for adsorption. After use in column (30 days) this material (15 g total) was treated in a fluidized bed reaction with 5 ml/g of NaOCl solution for 15 min. at a flow rate of about 60 ml per min. This carrier was then offered about 2700 IGIU/g which resulted in an observed (in-column) activity of 800 IGIU/g as opposed to 700 IGIU/g for new carrier offered the same amount/g of enzyme. After operational use, the carrier was treated with 5 ml/g of 5% NaOCl solution and offered 2700 IGIU/g enzyme resulting in only 542 IGIU/g activity. However, after a subsequent treatment with 13.3 ml/g of 5% NaOCl, the activity following identical enzyme immobilization was 864 IGIU/g.

The following table shows the relatively high level of loading activity observed after spent composite had been regenerated with varying amounts of a 5% NaOCl solution.

The original (unregenerated) carrier was initially offered 3500 IGIU/g of enzyme. After the regeneration step, the carriers were offered 2700 IGIU/g of enzyme. The regeneration step was accomplished by recirculating the indicated NaOCl solutions through approximately 15 g quantities of spent composite for about 120 minutes.

TABLE I

| Treatment (ml 5% NaOCl per Gram Carrier) | Initial Activity Using Regenerated Carrier (IGIU/g) |
| --- | --- |
| 5 | 651 |
| 10 | 709 |
| 13.3 | 809 |

After the above treatments, the carriers were rinsed in distilled water prior to adsorption of the enzyme. However, in a subsequent experiment, it was found that if enzymes were adsorbed to the carrier (no water rinse) after a 15 minute treatment with 5 ml/g of 5% NaOCl, the resulting activity of the composite having the regenerated carrier was 825 IGIU/gram.

TABLE II

Increasing the NaOCl treatment time did not increase effective enzyme loading.

| Time (min.) | NaOCl (%) | Amt. (ml sol'n/g) | Initial Activity (IGIU/g) |
| --- | --- | --- | --- |
| 120 | 5 | 5 | 799 |
| 15 | 5 | 5 | 810 |
| 15 | 5 | 5 | 797 |

No advantage was found in additional increase of the amount NaOCl used.

| 30 | 5 | 10 | 773 |
| 60 | 5 | 20 | 716 |

Varying the concentration and source (using commercial) household bleach) of NaOCl did not affect results.

| 15 | 2.5 | 10 | 774 |
| 15 | 5.75 | 5 | 807 |

Multiple Regenerations

Using a substantially similar MgO-Al$_2$O$_3$ carrier preparation (but from a different lot No.), the spent carriers were regenerated several times over as indicated below. As shown below, the same carrier preparation (about 15 g of 2.2% MgO, 97.8% Al$_2$O$_3$, 30 to 45 mesh, 190A avg. pore diameter) was regenerated four times with no observable loss in enzyme loading capability. In fact, a slight increase was noted.

As indicated, on the fifth regeneration attempt, the highest loading obtained after three attempts was 521 IGIU/g. At that point, the carrier was subjected to a pyrolysis treatment (600° C for 3 hours). Then, six more acceptable regenerations were performed using the NaOCl treatment. In all multiple regeneration experiments about 10 20 ml/g of 5% NaOCl was used for 15 min. at 25° C. in the "fluidized bed reactor" column. Approximately 15 g samples were regenerated initially with some carrier loss on subsequent regenerations.

TABLE III

| Regeneration Number | Initial Activity IGIU/g | Half-Life (days) 95% Confidence | | |
| --- | --- | --- | --- | --- |
| | | mean | LCL | UCL |
| 0 | 700 | 30 (Avg. value) | | |
| 1 | 793 | 23.5 | 22.0 | 25.1 |
| 2 | 905 | 27.9 | 26.1 | 29.9 |
| 3 | 789 | 41.3 | 37.6 | 46.0 |
| 4 | 713 | 31.7 | 24.7 | 44.2 |
| 5 | 521* | | | |
| | 874 | 34.9 | 32.7 | 37.3 |
| 6 | 835 | 29.9 | 28.0 | 32.0 |
| 7 | 796 | 27.4 | 24.4 | 31.3 |
| 8 | 673 | 36.5 | 32.4 | 41.6 |
| 9 | 787 | 33.8 | 30.7 | 37.6 |
| 10 | 600 | 21.6 | 19.0 | 25.1 |
| 11 | 706 | 19.5 | 16.5 | 23.8 |

*The maximum value of 521 IGIU/g was achieved after three regeneration attempts. Then the sample was pyrolyzed and regenerated 6 more times with the NaOCl solution as indicated.

EXAMPLE II

Glucoamylase Adsorbed to Recycled Al$_2$O$_3$ Carrier

In these experiments, glucoamylase was originally adsorbed on a porous alumina carrier (about 75 mg of enzyme offered per gram carrier). The carrier consisted of particles of porous alumina having an average particle size of about 30 to 45 mesh and an average pore diameter of about 270A. The glucoamylase enzyme activity unit ($E_o$), expressed as units (u) per gram composite, represents the enzyme activity capable of producing 1 u mole of glucose per min. at 60° C from a 30% starch solution.

A 5 gram sample (dry weight) of the immobilized glucoamylase composite was prepared by exposing wet carrier particles to 2.5 ml of an aqueous solution of the enzyme having an activity of 9000 u/ml for 180 min. at room temperature. After the exposure, the activity (u/g) of the composite was determined. A four gram sample of the composite was then contacted with 50 ml of a 5% NaOCl solution for 15–20 minutes in a 125 ml Erlenmeyer Flask to clean (regenerate) the carrier. Then, the regenerated carrier was again "loaded" with the same enzyme under similar enzyme immobilization conditions and the respective enzyme loading was again measured. The before and after results for 3 separate assays are shown in Table IV and indicate that the carrier could be recycled with the NaOCl treatment and that an immobilized enzyme composite could be made from spent composite regenerated with NaOCl solution in a simple batch-type reaction.

TABLE IV

| | Enzyme Activity ($E_o$ u/g) (before and after NaOCl treatment) | |
| --- | --- | --- |
| Assay No. | Before | After |
| 1 | 1945 | 1935 |
| 2 | 1976 | 1869 |
| 3 | 1977 | 1936 |
| Avg. | 1966 | 1913 |

EXAMPLE III

Lactase Adsorbed on Recycled Titania Carrier

In this example, composites of lactase adsorbed to porous titania particles (30 to 45 mesh, average pore diameter about 330A) were prepared by exposing about 10 g of the carrier to 20 ml of a solution of lactase enzymes having an activity of 500 u/ml. One unit of activity represents the capability of producing one u mole of glucose/min. at 50° C. from a 5% (wt.) lactose solution. The initial enzyme loading was determined for two samples. Each composite was then exposed to a commercially available household bleach solution (CHLOROX ®) by passing 2.5 liters of the solution 0.34% NaOCl) in a down flow through a packed column containing 9.4 grams of the composite. Enzymes were reloaded on each regenerated carrier under conditions similar to the original immobilization and activities were again determined. The results, summarized in the Table, indicate that immobilized enzymes can be prepared from regenerated carriers reacted with the NaOCl solution in a packed column.

TABLE V

| | Enzyme Activity $E_o$ u/g) Before and After NaOCl Treatment) | |
|---|---|---|
| Sample No. | Before | After |
| 1 | 404 | 423 |
| 2 | 362 | 408 |

EXAMPLE IV

Lactase Adsorbed on Recycled Silica Carrier

In this example, the support for a chemically coupled enzyme system was regenerated for subsequent reuse in an adsorbed system. The original immobilized enzyme composite comprised lactase enzymes coupled via intermediate silane and glutaraldehyde residues to porous silica particles having an average pore size of about 370A and particle size ranging from about 30 to 45 mesh.

The original composites were prepared by reacting 3 ml of a 10% aqueous solution of γ-aminopropyltriethoxysilane (A-1100, Union Carbide) per gram of silica to surface derivatize the inorganic carrier with organofunctional groups. These were modified for enzyme bonding by reaction with about 5 ml/g of a 2.5% glutaraldehyde solution. The modified product was then reacted with 2 ml/g of an aqueous solution of lactase enzymes having an activity of about 500 u/ml for about 150 min. at room temperature. Two 7.5 g samples were prepared and the initial enzyme activity was determined for each sample. The samples were then reacted with the NaOCl solution by pumping 2.5 l of 0.34% NaOCl solution through 7.5 g beds of the samples. These recycled supports were then exposed to an aqueous solution of the enzyme (15 ml having an activity of 420 u/ml) for 16 hours at room temperature to form an adsorbed immobilized enzyme system using a regenerated carrier. The activity of these samples was less than that of the original samples, indicating that the silane was now removed by the NaOCl. The results (Table VI) do show, however, that the recycled carrier could be used for an adsorbed system.

TABLE V

| Enzyme Activity $E_o$ u/g) Chemically Coupled System Before NaOCl Treatment vs. Adsorbed System After | | |
|---|---|---|
| Sample No. | Before | After |
| 1 | 548 | 294 |
| 2 | 517 | 299 |

Given the above disclosures, it is thought that numerous variations of our method of preparing immobilized enzymes using recycled carriers will occur to those skilled in the art. Accordingly, it is intended that the above examples should be construed as illustrative only and that the invention disclosed herein should be limited only by the following claims.

We claim:

1. A method of preparing an immobilized enzyme composite comprising enzymes bonded to porous, high surface area, insoluble support materials, the method comprising the steps of:
   a. reacting, with an aqueous solution of NaOCl, a spent immobilized enzyme composite comprising a porous, high surface area, insoluble inorganic support material having associated therewith contaminants resulting from use of the composite, the reaction being under conditions sufficient to cause the removal of substantially all such contaminants and to result in a reuseable enzyme support material; and
   B. reacting the reuseable enzyme support material of step (A) with an aqueous solution of active enzymes under conditions sufficient to bond at least some active enzymes onto the surface of the support.

2. The method of claim 1 wherein the reaction of step (B) comprises the step of bonding enzymes to the support by adsorption.

3. The method of claim 1 wherein the enzymes comprise glucose isomerase enzymes and the porous support comprises a MgO-Al$_2$O$_3$ material.

4. The method of claim 1 wherein the enzymes comprise glucoamylase enzymes and the porous support comprises an Al$_2$O$_3$ material.

5. The method of claim 1 wherein the enzymes comprise lactase enzymes and the porous support comprises a titania material.

6. The method of claim 1 wherein the enzymes comprise lactase and the porous support material comprises a silica material having residues of silane coupling agents associated on the surface thereof.

* * * * *

UNITED STATES PATENT OFFICE
CERTIFICATE OF CORRECTION

PATENT NO. : 4,087,330

DATED : May 2, 1978

INVENTOR(S) : Jerry L. Gregory and Wayne H. Pitcher, Jr.

It is certified that error appears in the above-identified patent and that said Letters Patent are hereby corrected as shown below:

Column 5, line 67, "10 20 ml/g" should be -- 10 to 20 ml/g --.

Column 8, line 3, "TABLE V" should be -- TABLE VI --.

Column 8, Claim 1, line 23, "a." should be -- A --.

Signed and Sealed this

Sixth Day of March 1979

[SEAL]

Attest:

RUTH C. MASON
Attesting Officer

DONALD W. BANNER
Commissioner of Patents and Trademarks